United States Patent [19]

Boehmke et al.

[11] Patent Number: 5,468,838
[45] Date of Patent: Nov. 21, 1995

[54] PROCESS FOR THE PREPARATION OF POLYSUCCINIMIDE, POLYASPARTIC ACID AND THEIR SALTS

[75] Inventors: Günther Boehmke; Gerd Schmitz, both of Leverkusen, Germany

[73] Assignee: Bayer AG, Leverkusen, Germany

[21] Appl. No.: 209,716

[22] Filed: Mar. 14, 1994

[30] Foreign Application Priority Data

Mar. 31, 1993 [DE] Germany ............... 43 10 503.3

[51] Int. Cl.$^6$ ............... C08G 73/10; C08G 85/00
[52] U.S. Cl. ............... 528/363; 524/548; 524/549; 524/599; 524/601; 524/606; 525/418; 525/419; 525/420; 528/328; 528/392
[58] Field of Search ............... 525/418, 419, 525/420; 528/328, 363, 392; 524/548, 549, 599, 601, 606

[56] References Cited

U.S. PATENT DOCUMENTS

| | | | |
|---|---|---|---|
| 3,846,380 | 11/1974 | Fujimoto et al. | |
| 4,590,260 | 5/1986 | Harada et al. | 528/328 |
| 4,696,981 | 9/1987 | Harada et al. | 525/328.2 |
| 4,839,461 | 6/1989 | Boehmke | 528/363 |
| 5,219,952 | 6/1993 | Koskan et al. | 525/419 |
| 5,288,783 | 2/1994 | Wood | 525/418 |
| 5,296,578 | 3/1994 | Koskan et al. | 528/363 |

FOREIGN PATENT DOCUMENTS 0578448  1/1994  European Pat. Off. .

OTHER PUBLICATIONS

Dessaignes, Quarterly Journal of the Chemical Society of London, vol. III, reprinted 1950, Translation of Comp. Rend. XXX, 324.
Dessaignes, Comp. Rend. XXXI, 432–433 (1850).
Kovacs et al., J. Org. Chem. 26, 1084 (1961).
Harada, Polycondensation of Thermal Precusors of Aspartic Acid, Journal of Org. Chem., vol. 24, pp. 1662–1666 (1959).

*Primary Examiner*—Shelley A. Dodson
*Attorney, Agent, or Firm*—Connolly & Hutz

[57] ABSTRACT

Polysuccinimide, polyaspartic acid and their salts are prepared by reaction of maleic anhydride and ammonia, polycondensation of the resulting product in the presence of a solubilizing agent and, if appropriate, hydrolysis.

12 Claims, No Drawings

PROCESS FOR THE PREPARATION OF POLYSUCCINIMIDE, POLYASPARTIC ACID AND THEIR SALTS

The invention relates to a process for the preparation of polysuccinimide (PSI) and polyaspartic acid and their salts in the presence of a solubilizing agent.

The preparation and use of polyaspartic acid (PAA) and its derivatives have been the subject matter of numerous publications and patents for a long time. The preparation can thus be carried out by thermal polycondensation of aspartic acid (J. Org. Chem. 26, 1084 (1961)).

U.S. Pat. No. 4,839,461 (= DE-A 3 626 6.72) describes the preparation of polyaspartic acid from maleic anhydride, water and ammonia. Maleic anhydride is converted into the monoammonium salt in an aqueous medium with addition of concentrated ammonia solution. In this process, the water must be evaporated out of the aqueous solution. The monoammonium salt is subjected to polycondensation to give PSI in the melt at temperatures of, for example, 125° to 140° C. Viscous phases which are difficult to control industrially are passed through during this procedure. In the course of the condensation, thermal insulation may occur, which severely delays heat transfer to end the reaction. Suitable apparatuses for detaching the wall layers and thorough mixing have therefore been proposed in that specification. For subsequent neutralization for preparation of salts, however, the mixture must again be converted into the liquid phase. This solution must be evaporated again for preparation of the solid salts.

It is known from U.S. Pat. No. 4,590,260 to subject amino acids to polycondensation together with derivatives of malic, maleic and/or fumaric acid at 100° to 225° C. According to U.S. Pat. No. 4,696,981, microwaves are employed in such reactions.

DE-A 2 253 190 (=U.S. Pat. No. 3,846,380) describes a process for the preparation of polyamino acid derivatives, specifically polyaspartic acid derivatives. According to this process, in addition to aspartic acid, maleic acid derivatives (the monoammonium salt and monoamide) are used by thermal polymerization for the preparation of the intermediate stage polysuccinimide, which in turn can be reacted with amines in suitable solvents to give the desired derivatives.

PAA can be employed, inter alia, as a fertilizer and against deposits and encrustations (see U.S. Pat. No. 4,839,461 and 5,116,513). Other known uses are, for example, a detergent additive (U.S. Pat. No. 4,839,461 and EP-A-454,126) and bone replacement materials (EP-A 383,568).

The invention is based on the object of providing an improved preparation process for polyaspartic acid.

The invention relates to a process for the preparation of polysuccinimide and polyaspartic acid and their salts by reaction of maleic anhydride or maleic acid, fumaric acid or mixtures thereof with ammonia, polymerization of the reaction product and, if appropriate, hydrolysis of the polymerization product to give polyaspartic acid or a salt thereof, which comprises carrying out the polymerization in the presence of a solubilizing agent.

A solubilizing agent (solubilizer) in the context of the present invention is understood as meaning a substance which improves the solubility of the ammonium salt of maleic acid in the polymerization melt, without itself being a solvent for this compound.

Because of the high reaction temperatures, solubilizing agents of high boiling point are preferred. The end product can also contain the solubilizing agent.

Suitable solubilizing agents are, in particular
1. acetamide,
2. hydroxyethylamides of $C_8$–$C_{12}$-fatty acids,
3. oxyethylation products of $C_{10}$–$C_{18}$-fatty acid amides with 20 to 100 EO chains,
4. ethylene oxide adducts of $C_{10}$–$C_{18}$-fatty alcohols with 20 to 100 EO chains and polyethylene glycols having molecular weights of 150 to 2000.

They are employed in amounts of 10 to 100% by weight, preferably 20 to 70% by weight, based on the calculated end yield. The solubilizing agents based on the oxyethylated fatty alcohols and fatty acid amides allow removal of a larger portion of the solubilizing agent after the neutralization and its re-use in a subsequent batch, while the salt layer is used with the remainder of the solubilizing agent or is passed for spray drying beforehand.

The liquid solubilizing agents are preferably used if a liquid formulation is to be used. Solid adducts, of 50 to 100 mol of ethylene oxide with fatty alcohol or fatty acid amides, can be dried and sprayed after neutralization has ended or flaked off on a cooling roll. These end products have outstanding properties as dispersing agents and as an additive to detergents, since the good properties of the polyaspartic acid salts are assisted and in some cases even intensified by nonionic surfactants.

In a preferred embodiment, maleic anhydride or maleic acid, fumaric acid or mixtures thereof and ammonia are reacted in a molar ratio of 1:1 to 1.5 and the polymerization is carried out at 120° to 240° C. in particular 125° to 180° C., and very particularly preferably at 125°–145° C. After the polymerization, the melt obtained can be cooled to 80° to 120° C. and neutralized by addition of aqueous solutions or suspensions of metal hydroxides or ammonium hydroxides. The solubilizing agent can be recovered again after the neutralization.

In a preferred embodiment, the polymerization is carried out in a suitable reactor for continuous operation (paddle drier, single-shaft and twin-shaft high viscosity reactors, for example Discotherm and All-Phase Konti apparatuses from List, screw machines, preferably self-cleaning multishaft screws, or in a belt reactor) in the form of a continuous thermal short-time polymerization with a residence time of 0.5 to 30 minutes, preferably 1.5 to 15 minutes.

In a preferred embodiment, the resulting polyaspartic acid and its salt are spray dried.

The use of the solubilizing agents also has a positive effect on the troublesome sublimation of maleic anhydride, since it practically no longer occurs. At the same time, the distillative removal of the water of solution and reaction is converted into uniform boiling without shocks and foaming by the hydrophilic solubilizing agents.

The risk of local overheating is also eliminated with the improved heat transfer.

The aspartic acid in the present invention is understood as meaning both free polyaspartic acid and its salts.

In a preferred embodiment, the polyaspartic acid prepared according to the invention essentially comprises recurring units of the following structure:

a) 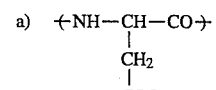

and b) 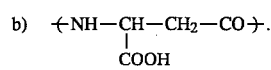

In addition to the recurring polyaspartic acid units a) and b), the product can comprise the following recurring units:
c) malic acid units of the formula

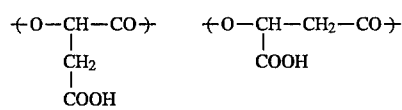

The chemical structure is preferably analyzed by $^{13}$C—NMR and, after total hydrolysis, by HPLC, GC and GC/MS.

Both the abovementioned recurring units a) and b) and, at the same time, the imide structures prepared by splitting off H$_2$O can be present in the product obtained directly in the polymerization or hydrolysis.

It is assumed that the following structures are passed through in the reaction according to the invention:

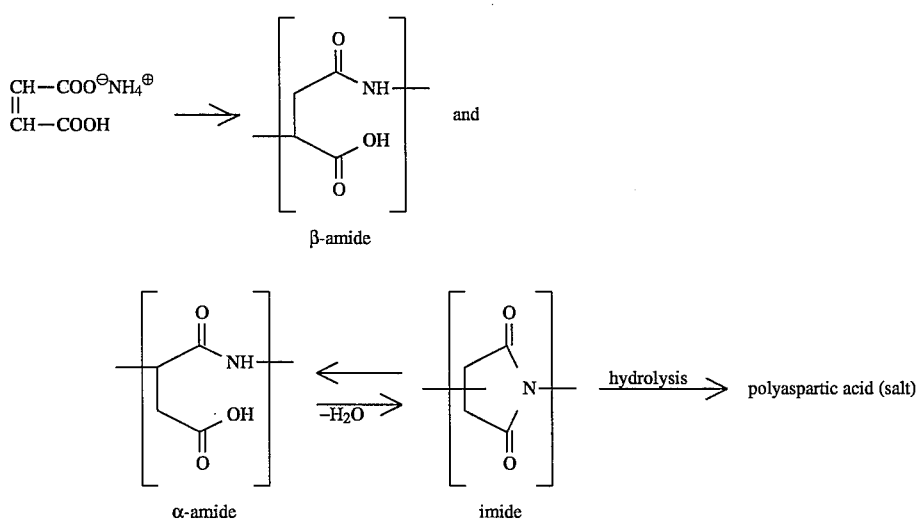

The polymer prepared displays different chain lengths or molecular weights according to analysis by gel permeation chromatography (Mw=500 to 10000, preferably 1000 to 5000, particularly preferably 2000 to 4000), depending on the reaction conditions, for example residence time and temperature of the thermal polymerization.

The compounds prepared according to the invention, above all the ammonium and alkali metal salts, are used in particular with solubilizing agent in detergents to improve the washing result in hard water and to prevent graying and encrustation of the washed goods, and furthermore as dispersing agents, preferably in plant protection agents and optical brightener formulations.

EXAMPLE 1

98 g of maleic anhydride and 18 g of water, as well as 70 g of an ethylene oxide adduct of tallow fatty alcohol, a mixture of saturated and unsaturated C$_{16}$–C$_{18}$-fatty alcohols with 50 mol of EO, are melted in a stirred flask. The temperature is adjusted to 60° to 70° C. 1 mol of ammonia solution (=68 g of 25% strength solution) is allowed to run into this mixture such that no ammonia can escape. The solution of the acid ammonium salt of maleic acid is dehydrated by heating to 110° to 120° C. A slight vacuum can accelerate the removal of the water. For the polycondensation, the temperature is increased to 130° to 140° C. After 2 hours, the temperature is increased to 140° to 145° C. A sample can be taken within 1 to 2 hours. The slightly brownish-colored mass is readily stirrable and solidifies below 50° C. The yield is 180 g.

For the neutralization, 482 mg of KOH are consumed per 1.64 g of the melt. The batch can be converted into the form of scales via a cooling roll. Before use, the necessary amount of alkali, for example sodium carbonate, is expediently admixed.

EXAMPLE 2

To prepare the sodium salt, the batch according to Example 1 is repeated and brought to the end of the polycondensation. The melt is cooled to 100° to 110° C. and neutralized by addition of about 78 to 80 g of 45% strength sodium hydroxide solution. The water can be distilled off under a weak vacuum. A scale form of the sodium salt of polyaspartic acid with a content of about 70 to 75% can again be obtained from the melt via a cooling roll.

This product with the solubilizing agent is outstandingly suitable as an additive to detergents based on Na alkylbenzenesulfonate instead of sodium tripolyphosphate and additional polymers for improving the washing effect in hard water and preventing the graying effect on the washed goods.

This mixture furthermore is a very active, degradable dispersing agent for pulverulent plant protection formulations.

EXAMPLE 3

70 g of an adduct of 55 mol of ethylene oxide with oleic acid monoethanolamide, 18 g of water and 98 g of maleic anhydride are melted in a stirred flask. The acid ammonium salt of maleic acid is prepared with 1.1 mol of ammonia solution (=75 g of 25% strength solution) under a nitrogen atmosphere. The anhydrous melt is obtained therefrom by distillation of the water up to 120° C. The polycondensation is initiated by increasing the temperature to 135° C. and maintaining it at this level for 2 hours. The polycondensation is brought to completion at 140° to 150° C. for a further 1–3 hours.

A slight vacuum accelerates removal of the water of reaction.

A sample of 1.82 g consumes 485 mg of KOH.

After cooling to 100° to 110° C., the batch is neutralized with about 80 g of a 45% strength sodium hydroxide solution. Stirring is switched off at 80° to 90° C. and the batch is left to stand to separate. Within 30 to 60 minutes, a lower aqueous salt solution and an upper, water-containing emulsifier layer (oleic acid amide+56 EO) have settled. The upper layer, with about 60 g of the emulsifier, can be used for further batches, while the lower aqueous solution of the sodium salt of polyaspartic acid, with about 10 g of emulsifier, can be employed directly for spray drying. This salt, with the residual solubilizing agent, is outstandingly suitable for use in pulverulent detergents and plant protection formulations.

EXAMPLE 4

40 g of triethylene glycol are employed as the solubilizing agent in a batch according to the figures of Example 1. When the condensation has ended, the batch is cooled to 80° C. and neutralized with about 113 g of a 30% strength sodium hydroxide solution. A 50% strength solution results, which is advantageously suitable for liquid formulations of detergents.

EXAMPLE 5

98 g of maleic anhydride, 18 g of water and 50 g of an adduct of 30 mol of ethylene oxide with coconut fatty alcohol ($C_{10}$–$C_{14}$-alcohol) are reacted in a stirred flask by the process of Example 1. After cooling to 90° to 100° C., 40 g of water and 60 g of monoethanolamine are added and the mixture is subsequently stirred at this temperature for a further hour. A liquid formulation of the monoethanolamine salt of polyaspartic acid is obtained.

We claim:

1. A process for the preparation of polysuccinimide by reaction of maleic anhydride or maleic acid, fumaric acid or mixtures thereof with ammonia and polymerization of the reaction product, which comprises carrying out the polymerization in the presence of a solubilizing agent.

2. The process as claimed in claim 1, wherein the solubilizing agent is acetamide, a hydroxyethylamide of a $C_8$–$C_{12}$-fatty acid, an oxyethylation product of a $C_{10}$–$C_{18}$-fatty acid amide or an ethylene oxide adduct of a $C_{10}$–$C_{18}$-fatty alcohol or polyethylene glycols.

3. The process as claimed in claim 1, wherein maleic acid and ammonia are reacted in a molar ratio of 1:1 to 1.5.

4. The process as claimed in claim 1, wherein the polymerization is carried out at 120° to 240° C.

5. A process for the preparation of polyaspartic acid and salts thereof by reaction of maleic anhydride or maleic acid, fumaric acid or mixtures thereof with ammonia, polymerization of the reaction product and hydrolysis of the polymerization product to give polyaspartic acid or a salt thereof, which comprises carrying out the polymerization in the presence of a solubilizing agent.

6. The process as claimed in claim 5, wherein the solubilizing agent is acetamide, a hydroxyethylamide of a $C_8$–$C_{12}$-fatty acid, an oxyethylation product of a $C_{10}$–$C_{18}$-fatty acid amide or an ethylene oxide adduct of a $C_{10}$–$C_{18}$-fatty alcohol or polyethylene glycols.

7. The process as claimed in claim 5, wherein maleic acid and ammonia are reacted in a molar ratio of 1:1 to 1.5.

8. The process as claimed in claim 5, wherein the polymerization is carried out at 120° to 240° C.

9. The process as claimed in claim 1, wherein the polymerization is carried out at 120° to 150° C.

10. The process as claimed in claim 1, wherein the polymerization is carried out at 125° to 145° C.

11. The process as claimed in claim 5, wherein the polymerization is carried out at 120° to 150° C.

12. The process as claimed in claim 5, wherein the polymerization is carried out at 125° to 145° C.

* * * * *